United States Patent [19]
Yada et al.

[11] Patent Number: 5,215,773
[45] Date of Patent: Jun. 1, 1993

[54] METHOD FOR DETERMINING PROCESSING QUALITY OF STARCHY VEGETABLES

[75] Inventors: Rickey Y. Yada; Valerie Smith, both of Guelph; David Stanley, Rockwood; Robert H. Coffin, Kensington; Michael J. Leszkowiat, Mississauga, all of Canada

[73] Assignee: The University of Guelph, Guelph

[21] Appl. No.: 587,681

[22] Filed: Sep. 25, 1990

[51] Int. Cl.$^5$ .............................................. G01N 33/00
[52] U.S. Cl. .................................... 426/231; 426/523
[58] Field of Search ............... 426/231, 661, 615, 637, 426/523

[56] References Cited

U.S. PATENT DOCUMENTS 4,743,455  5/1988  Nichols ............................... 426/233

OTHER PUBLICATIONS

"Activities Of Enzymes Of Sugar Metabolism In Cold-Stored Tubers Of *Solanum Tuberosum*", by Pollock and Rees, pp. 613–617.
"Respiratory Enzyme Activity in Low Temperature Sweetening of Susceptible and Resistant Potatoes", by Barichello et al. pp. 1060–1063.
"Thermal Properties of the Starch/Water System", by Stevens and Elton, pp. 8–11.
"Application of Differential Scanning Calorimetry to Starch Gelatinization", by Wootton aned Bamunuarachchi, pp. 201–204, 262–264.
"Phase Transitions of the Starch-Water System", by Donovan, pp. 263–275.
"Starch Gelatinization Phenomena Studied by Differential Scanning Calorimetry", by Biliaderis et al, pp. 1669–1674.
"Polysaccharide-Water Interactions—Thermal Behavior Of Rice Starch", by Maurice et al, pp. 211–227.
"Applications of Differential Scanning Calorimetry in Foods", by Lund, pp. 125–143.
"Biochemical-Physical Characteristics and Processing Quality Of Field and Storage-Type Potatoes", by Leszkowiat, pp. 1–111.
"Studies on the Functional Characteristics and Digestibility of Starches from *Phaseolus vulgaris* Biotypes", by Hoover et al.
"Effect of Low Temperature Storage on Sugar Concentrations and Chip Color of Certain Processing Potato Cultivars and Selections", by Coffin et al, pp. 639–645.
"HPLC Determination of Fructose, Glucose, and Sucrose in Potatoes", by Wilson, et al, pp. 300–301.
"Starch Gelantinization in Cold Temperature Sweetening Resistant Potatoes", by Leszkowiat, et al, pp. 1338–1340.
"Thermal Characterization of Rice Starches: A Polymeric Approach to Phase Transitions of Granular Starch", by Biliaderis, et al., pp. 6–14.
"Isolation and Characterization Of Amyloplast Envelope Membranes From *Solanum Tuberosum*", by Fishwick et al, pp. 55–59.

*Primary Examiner*—George Yeung
*Attorney, Agent, or Firm*—Bell, Seltzer, Park & Gibson

[57] ABSTRACT

A method is provided for selecting starch-containing vegetables which are subject to low temperature sweetening based on the quality of product to be derived from said vegetables when processed in a manner which can result in undesirable product coloration due to chemical changes of surface sugars on the prepared product, a predetermined minimum level of starch granule crystallinity being established for the vegetable to be processed, above which minimal level an acceptable quality of processed product having an acceptable level of coloration is assured. The method comprises measuring starch granule crystallinity of the vegetable to be processed and selecting for later processing vegetables having a measured starch granule crystallinity above a predetermined minimum level which indicates that the vegetable will resist low temperature sweetening.

8 Claims, 5 Drawing Sheets

METHOD FOR DETERMINING PROCESSING QUALITY OF STARCHY VEGETABLES

FIELD OF THE INVENTION

This invention relates to the processing of starch-containing vegetables to provide chip products, which includes chips, french fries, snacks and the like. More particularly, it relates to a method for predicting processing quality of such vegetables.

BACKGROUND OF THE INVENTION

When chip products are prepared from starch-containing vegetables, excessive sugar levels in the vegetable can lead to an unacceptable dark colouration of the chips on cooking, due to non-enzymatic browning arising from caramelisation of sugars on the surface of the chip products and Maillard browning due to reaction of sugars and amino acids.

Various methods of extracting excess sugar from vegetable slices before cooking have been used to overcome this problem. For example, U.S. Pat. No. 4,743,455 to Nichols discloses a method for blanching raw potato slices before chip production.

Such methods may remove valuable nutrients along with excess sugar and may affect the texture or quality of the final product.

It is preferable to use vegetables having sugar levels which will not cause a discoloration problem.

However, even vegetables which have satisfactory sugar levels at harvest may undergo low-temperature sweetening or chill-sweetening when stored at low temperatures, due to conversion of starch to free sugars, resulting in unacceptably high sugar levels after storage. Vegetables subject to chill-sweetening include potatoes, carrots, cassava and sweet potatoes.

Chill-sweetening of a crop such as potatoes can cause substantial losses to growers and processors.

Since chill-sweetening of potatoes becomes significant below 10° C., potatoes are generally stored at 12° C. in the french fry and potato chip industries. At this temperature, however, dry matter loss occurs during storage and steps must be taken to control sprouting, usually by spraying with sprout inhibitors. Different potato cultivars vary widely in their susceptibility to chill-sweetening.

If this susceptibility could be determined, and if cultivars resistant to chill-sweetening could be identified, lower storage temperatures and better identification of batches and selections of crop suitable for storage would be possible.

No suitable method has been available, however, to permit such a determination.

Previous workers had suggested that cold lability of glycolytic enzymes led to decreased sugar metabolism and hence chill-sweetening Pollock, C. J. and Rees, T. (1975) *Phytochemistry*, vol. 14, p. 613. As already mentioned, this is undesirable due to various reactions of sugars on the product surface during the cooking process.

Examination of the respiratory enzyme activities of chill-sweetening-susceptible and -resistant potato cultivars has, however, shown that these enzymes play little or no role Barichello, V. et al. (1990) *Journal of Food Science*, vol. 55, p. 1060.

Differential Scanning Calorimetry (DSC) has been used to study the effect of various manipulations on the gelatinisation of starches Stevens, D. J. et al. (1971) *Die Starke*, vol. 23, p. 8; Wooton, M. et al. (1979) *Starch-Starke*, vol. 31, p. 201; Wooton, M. et al. (1979) *Starch-Starke*, vol. 31, p. 262; Donovan, J. W. (1979) *Biopolymers*, vol. 18, p. 263; Biliaderis, C. G. et al. (1980) *Journal of Food Science*, vol. 45, p. 1669; Morise, T. J. et al. (1985) "Properties of Water in foods" (eds. Simatos and Multon) p. 211; Lund, D. B. (1983) "Physical Properties of Foods" (eds. Peleg and Bagley). DSC scans of native starch from various species including potatoes have been compared, as well as the effect of chemical modifications of wheat starches on their DSC profiles Wooton et al., page 201, supra, and Wooton et al., page 262, supra.

Donovan supra has studied DSC endotherms of purified potato starch granules in the presence of different concentrations of water and has proposed mechanisms for the physico-chemical changes occurring on gelatinisation. Further efforts to characterise the physico-chemical changes of starch gelatinisation have been described by Biliaderis et al supra.

Maurice et al. supra have used DSC to examine the effects of heat treatment at various times, temperatures and water contents on rice and waxy maize starch.

Lund supra has examined the effect on gelatinisation of different proportions of amylose and amylopectin in starch using DSC techniques.

Prior to the present invention, the emphasis in chill-sweetening studies was on enzyme patterns and it was not suspected that starch granule structure and stability was important in this phenomemon.

It was not expected that DSC profiles, which reflect such starch granule characteristics, could be used to indicate the suitability of starch-containing vegetables for chip preparation free of discolouration problems and to provide an indicator of susceptibility to chill-sweetening in starchy vegetables subject to this problem.

SUMMARY OF THE INVENTION

In accordance with one embodiment of the invention, a method of determining the processing quality of starch-containing vegetables is provided which comprises measuring the starch granule stability of the vegetables.

In accordance with a further embodiment, a method of determining the chipping suitability of starch-containing vegetables is provided which comprises measuring the starch granule stability of the vegetables.

In accordance with a further embodiment, a method of determining the susceptibility of vegetables to low temperature-sweetening is provided which comprises measuring the starch granule stability of the vegetables.

In accordance with a further embodiment, a method for accepting starch-containing vegetables which are subject to low-temperature sweetening is provided which is based on the quality of product to be derived from the vegetables when processed in a manner which can result in undesirable product colouration due to chemical changes of surface sugars on the prepared product, a predetermined minimum level of starch granule stability being established for the vegetable to be processed, above which minimum level an acceptable quality of processed product having an acceptable level of colouration is assured, the method comprising:

(i) measuring starch granule stability of the vegetable to be processed; and (ii) accepting for later processing the vegetable having the measured starch granule stability above the predetermined minimum level by virtue of the accepted vegetable having the measured starch granule stability of the minimum level resisting low temperature sweetening.

The phrase "starch granule stability" as used herein means all characteristics of starch granule composition and compactness of aggregation which are reflected in the DSC profile of the starch. Such characteristics may be measured by techniques other than DSC, for example by x-ray diffraction which is a very expensive alternative.

"Chipping suitability" of vegetables as used herein means having acceptable Agtron colour scores when processed into chips by standard methods.

SUMMARY OF DRAWINGS

The invention, as exemplified by preferred embodiments, is described with reference to the drawings in which.

DETAILED DESCRIPTION

The molecules of starch in starchy vegetables are arranged into macromolecular aggregates called starch granules. It is generally accepted that a starch granule is a semi-crystalline entity (spherulite) which contains both crystalline and amorphous regions Biliaderis, (1980) *Journal of Food Science*, supra. Several characteristics of the starch granule are determined by the extent to which the starch molecules are of a crystalline nature in the granule. We have found that the degree of crystallinity and hence degree of ordered compactness of starch molecules in the starch granules can be related to the extent to which starchy vegetables are subject to chill-sweetening. We have discovered that the use of Differential Scanning Calorimetry (DSC) can be accurately relied upon to determine the degree of crystallinity of the starch granules in any type of starchy vegetable. We have determined that such predictability is based on the principle that when starch granules are heated in the presence of water, gelatinisation occurs, associated with loss of crystallinity and swelling of the granules as amorphous regions of the granule take up water.

Figure 1:
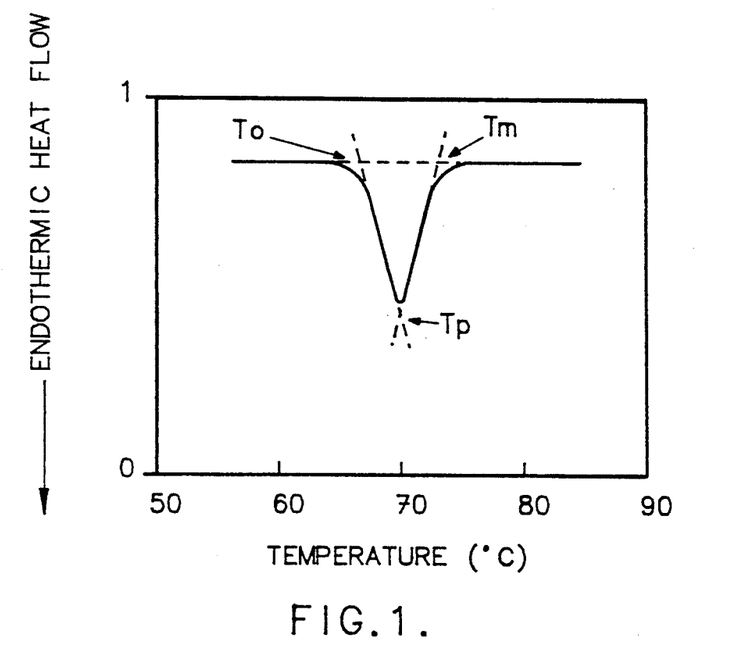
FIG. 1 is a DSC curve for the gelatinisation of starch.

We have found that the physical changes accompanying gelatinisation are reflected in the profiles obtained by DSC, as demonstrated in FIG. 1, which shows gelatinisation of isolated and intact potato starch. At $T_o$, gelatinisation onset, the amorphous regions of the starch begin to take up water Movise et al., supra. $T_p$, the peak temperature, occurs at the maximum gain of entropy when amorphous regions swell and disrupt crystallites, facilitating their melting Biliaderis et al., (1980) *Journal of Food Science*, supra. The final temperature, $T_m$, indicates the "melting" of the crystallites Morise et al., supra. The greater the degree of crystallinity in the starch granule, the greater the gain in entropy of the DSC analysis and hence the greater $T_p$, required to disrupt crystallinity. When the mole ratio of water to starch is greater than 4, only the single endotherm of FIG. 1 is obtained by DSC Donovan, supra.

The values of the DSC thermal parameters $T_o$, $T_p$ and $T_m$ therefore reflect the stability and degree of organization of the starch granules. This aspect was also investigated by others (see Donovan, supra; Biliaderis et al., (1980) *Journal of Food Science*, supra; Leszkowiat, M. J. (1988) M. Sc. Thesis, University of Guelph; and Hoover, R. et al., (1985) *Staerke*, vol. 37, p. 181) where such work as in Donovan discusses the concept of "degree of crystallinity".

Figure 2A:
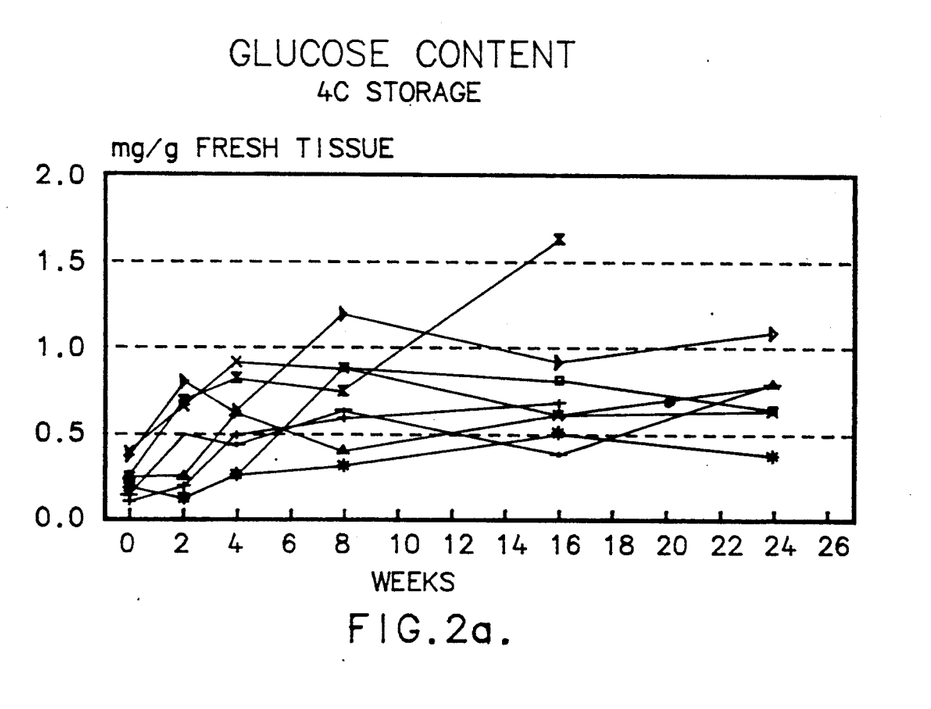
FIGS. 2a–2c show the glucose, fructose and sucrose content in mg/g fresh tissue of potato cultivars Norchip (·); ND 860-2 (*); Atlantic (|); Chieftan ($\bar{X}$); Russet Burbank (x); Saginaw Gold (□); Onaway (◇) and Shepody (Δ) stored at 4° C.
Figure 2B:
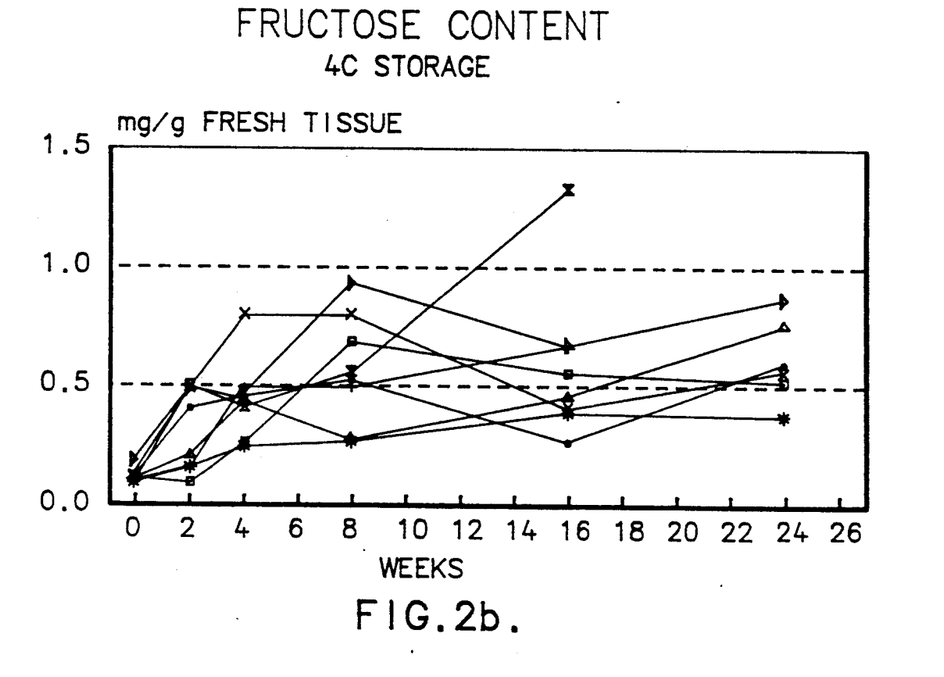
Figure 2C:
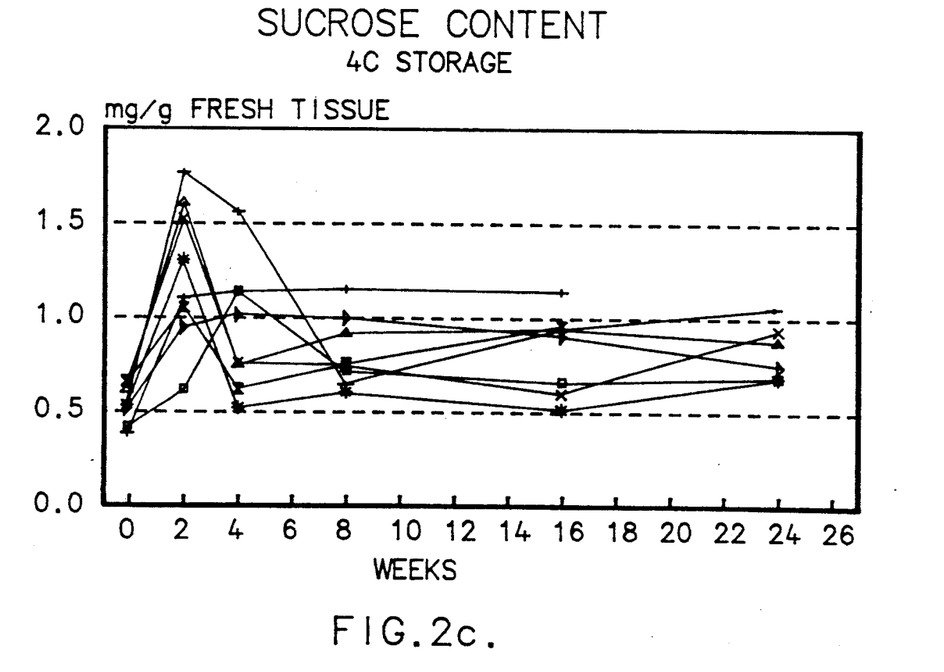
Figure 3A:
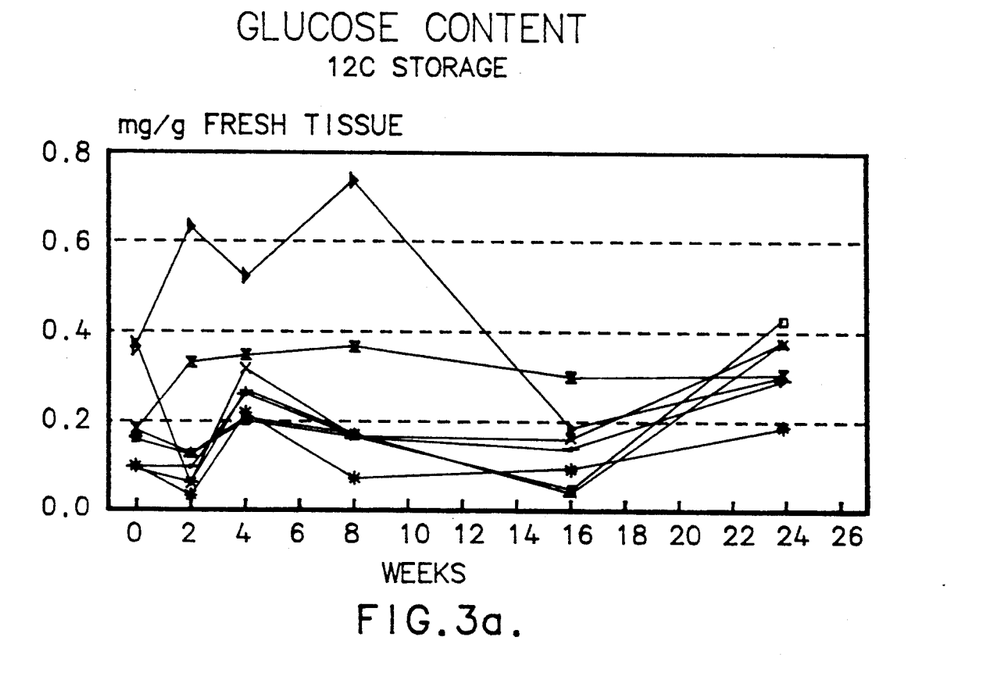
FIGS. 3a–3c show the glucose, fructose and sucrose content in mg/g fresh tissue of potato cultivars Norchip (·); ND 860-2 (*); Atlantic (|); Chieftan ($\bar{X}$); Russet Burbank (x); Saginaw Gold (□); Onaway (◇) and Shepody (Δ) stored at 12° C.
Figure 3B:
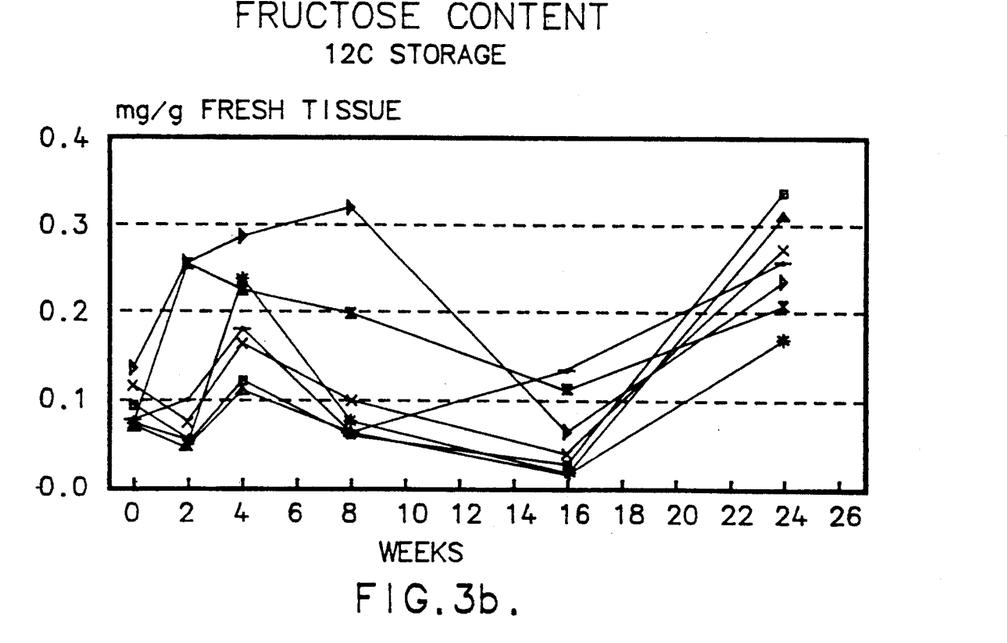
Figure 3C:
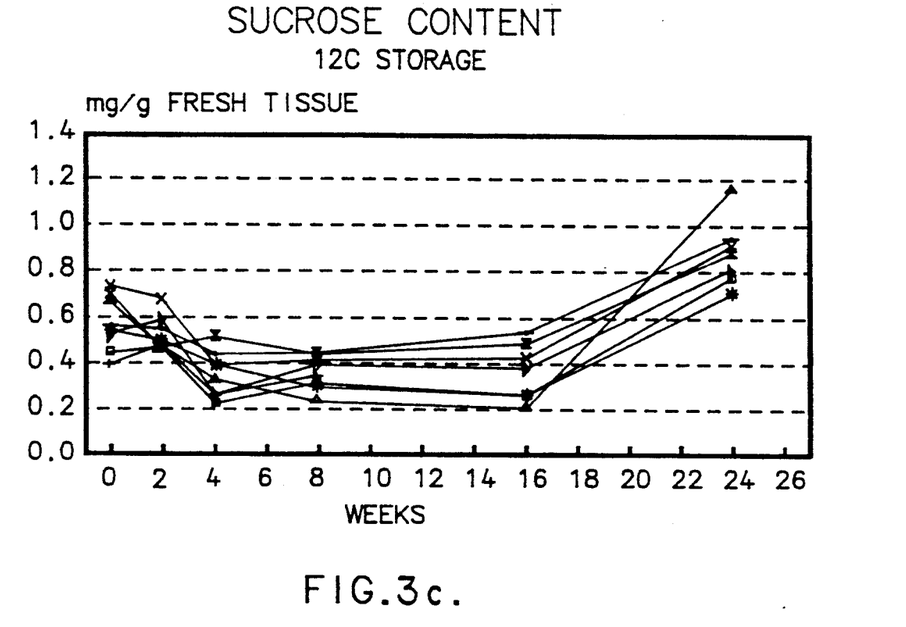
Figure 4A:
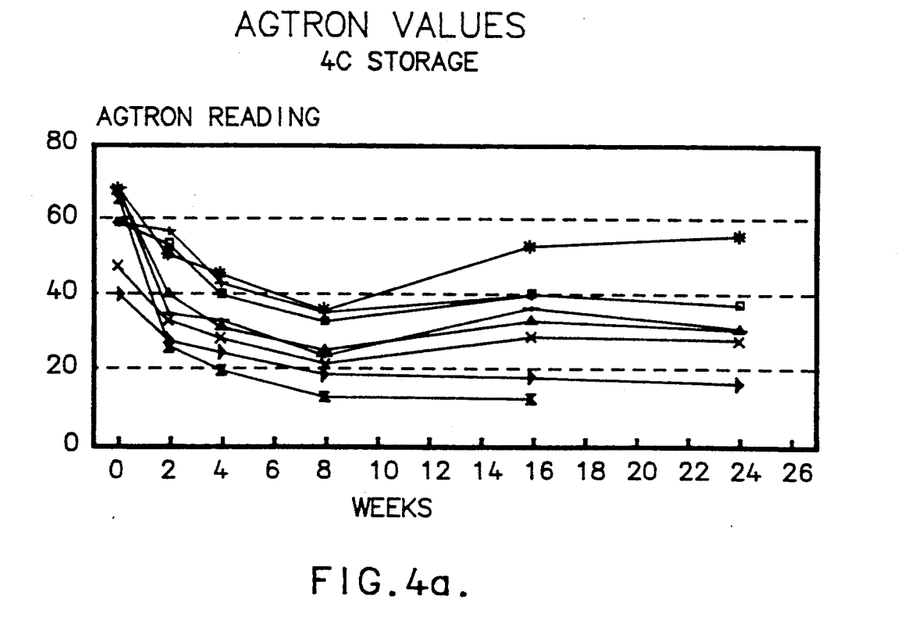
FIGS. 4a and 4b show Agtron values for potato cultivars Norchip (·); ND 860-2 (*); Atlantic (|); Chieftan ($\bar{X}$); Russet Burbank (x); Saginaw Gold (□); Onaway (◇) and Shepody (Δ) stored at 4° C. (panel A) and 12° C. (panel B)
Figure 4B:
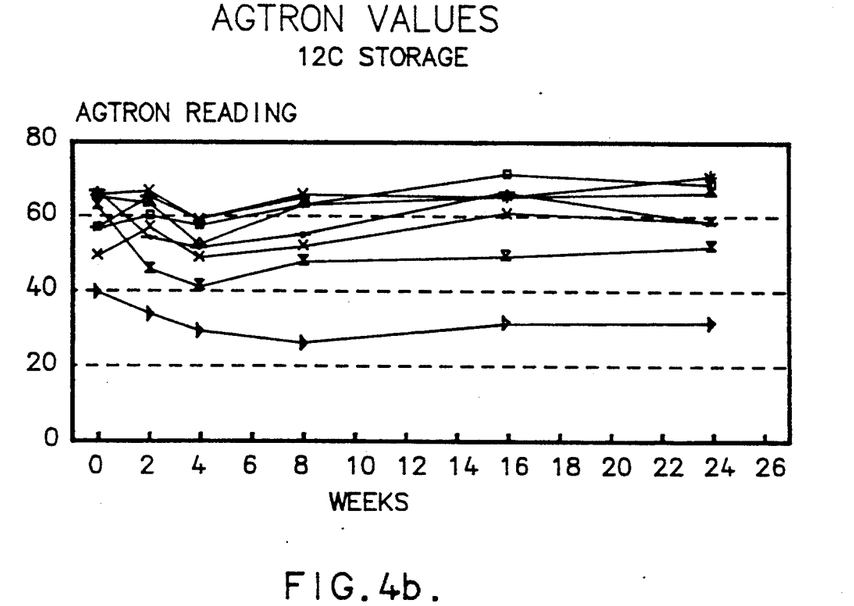

The impact of starch granule stability (i.e. the degree of crystallinity) in the starchy vegetable on vegetable processability has not been contemplated. We have discovered that there is a relationship between the two. We took thirteen potato cultivars which chill-sweeten to varying degrees and examined them during storage at either 4° C. or 12° C. for 24 weeks. Glucose, fructose and sucrose content after various lengths of storage are shown in FIGS. 2 and 3. ND 860-2, a chill-sweetening resistant cultivar, had significantly lower sugar content, and Onaway and Chieftan significantly higher, at both storage temperatures as compared to the other varieties. ND 860-2 produced chips of acceptable colour for the entire storage period both at 4° C. and 12° C., with the exception of one sample stored at 4° C. for 8 weeks, as seen in FIG. 4. In contrast, Onaway at no time produced acceptable coloured chips and Chieftan did so only at harvest. Remaining cultivars fell in the range between these extremes.

The DSC thermal parameters of potato tissue samples taken at time of harvest from the same thirteen cultivars are shown in Table 1.

TABLE 1

Starch gelatinization characteristics of potato tissue isolated from various cultivars/selections.

| Cultivar/ Selection | | Initial Thermal Curve | |
|---|---|---|---|
| | $T_o$ (°C.) | $T_p$ (°C.) | $T_m$ (°C.) |
| Norchip | 70.4 (0.3)[1]bc[2] | 73.3 (0.3)bcd | 76.6 (0.4)cd |
| ND 860-2 | 73.6 (0.4)a | 76.3 (0.4)a | 79.8 (0.7)a |
| Atlantic | 71.6 (0.2)b | 74.7 (0.5)ab | 77.9 (1.0)bc |
| Chieftan | 68.3 (1.1)d | 71.9 (0.9)de | 75.7 (1.0)d |
| Russet Burbank | 69.2 (0.4)cd | 72.2 (0.4)cde | 76.3 (0.3)cd |
| Saginaw Gold | 70.8 (0.7)bc | 73.8 (0.6)bc | 77.9 (0.1)bc |
| Onaway | 68.4 (0.1)d | 71.4 (0.1)e | 75.1 (0.2)d |
| Shepody | 70.6 (0.7)bc | 73.6 (0.6)bcd | 77.4 (0.2)bc |
| GJ 857-1 | 71.5 (1.3)b | 75.0 (1.6)ab | 79.8 (1.6)a |
| GJ 853-2 | 71.1 (1.7)b | 74.5 (1.6)b | 79.0 (1.0)ab |
| GJ 853-36 | 70.2 (1.2)bc | 73.2 (0.9)bcd | 77.7 (0.8)bc |
| GJ 853-1 | 71.1 (2.0)b | 74.3 (2.1)b | 78.3 (1.8)ab |
| GJ 8540-2 | 70.7 (0.6)bc | 73.7 (0.4)bcd | 78.3 (0.6)ab |

[1]Each number in parentheses is the standard deviation of the mean (n = 3).
[2]Means with the same letter are not significantly different (P > 0.05) by Duncan's new multiple range test.

ND 860-2 had the highest values fox $T_o$, $T_p$ and $T_m$, Onaway and Chieftan had the lowest and other cultivars had intermediate values.

Unexpectedly, we have found that the DSC thermal parameters of a potato cultivar measured at time of harvest indicates the susceptibility or resistance of that cultivar to chill-sweetening on storage at low temperatures and hence its processibility. This is thought to be due primarily to the principle that the degree of starch granule stability determines the extent to which starch granules are broken down to produce sugars. The greater the degree of starch granule stability, the lesser amount of sugars formed during low temperature (i.e. below 10° C.) storage of the potatoes.

Peak temperature, $T_p$, was also compared to chip colour score or Agtron value for each cultivar and the results are shown in Table 2.

TABLE 2

| Cultivar/Selection | $T_p$ (°C.) | Average Agtron Value Throughout Storage |
|---|---|---|
| Norchip | 73.3 (0.3)[1] | 46.15 |
| ND 860-2 | 76.3 (0.4) | 57.16 |
| Atlantic | 74.7 (0.5) | 52.05 |
| Chieftan | 71.9 (0.9) | 36.83 |
| Russet Burbank | 72.2 (0.4) | 41.82 |
| Saginaw Gold | 73.8 (0.6) | 52.53 |
| Onaway | 71.4 (0.1) | 26.51 |
| Shepody | 73.6 (0.6) | 47.94 |

[1]Each number in parentheses is the standard deviation of the mean (n = 3). Correlation coefficient r = 0.911, P ≤ 0.01.

There was a significant correlation between peak temperature, $T_p$, determined by DSC and chip colour score. Since DSC provides a measurement of starch granule stability and starch granule structure (i.e. the degree of crystallinity in the starch granule), the unexpected high correlation between DSC peak temperature and chip colour scores indicates that these starch properties are important factors in determining the extent of chill-sweetening of potatoes. As previously discussed, surface sugars are not desired because of a darkened product developed during a deep frying in hot oil or baking process. However, in accordance with this invention, the extent of chill-sweetening can now be predicted by determining the starch granule stability. The greater the stability, the less chill-sweetening will occur so that there will be less surface sugars in vegetables which have a higher degree of starch granule stability. From these results, the minimum peak temperature can be established. All potatoes which are suitable for processing have a peak temperature by DSC analysis equal to or greater than the minimum peak temperature. From the results of Table 2 and FIG. 5, the minimum peak temperature is 73.7° C.

The invention provides a novel and convenient method of determining the chipping suitability of potatoes and other starch-containing vegetables and of predicting their susceptibility or resistance to low-temperature sweetening.

The ability to determine conveniently cultivars or batches of potatoes which are resistant to chill-sweetening in the range of 1° C. to 10° C. will permit wider use of this temperature for commercial potato storage. Storage around 4° C. will obviate the need to use sprout inhibitors and will improve product quality by better maintaining dry matter content. Winter transportation of potatoes will be simpler and less energy-consuming if loads do not have to be maintained above 10° C. Improved storage will also reduce dependence on imported potatoes.

EXAMPLE 1

Sugar Content During Storage

Mature tubers of Norchip, Atlantic, Shepody, Chieftan, Onaway, Saginaw Gold, Russet Burbank and the selections ND 860-2, GJ 857-1, GJ 853-3, GJ 853-36, GJ 853-1 and GJ 8540-2 were obtained from the Cambridge Agriculture Research Station, Ontario Ministry of Agriculture and Food, Cambridge, Ontario. Potatoes were grown using standard agronomic practices Coffin, R. H. et al., (1987) Journal of Food Science, vol. 52, p. 639. Potato tubers were hand-harvested 14 days after foliar senescence, cured for 14 days at 15° C., divided into equal lots and stored at 4° C. or 12° C. for 24 weeks at 90–95% relative humidity.

For each cultivar/selection, triplicate 100 g samples were taken from representative tubers and placed in a Braun juicer (Braun Canada Limited, Mississauga, Ontario). Juice was collected and an equal volume of methanol was added. Sugar analysis was performed in triplicate for each treatment according to the HPLC method of Wilson et al (1981) Journal of Food Science, vol. 46, p. 300. Results as described earlier are set out in FIGS. 2 and 3.

EXAMPLE 2

Chip Colour Scores During Storage

Potato cultivars/selections were grown and harvested as in Example 1. A composite chip sample for each cultivar/selection treatment was prepared from 8 representative tubers which were peeled and sliced into 3 mm cross sections using an automatic slicer. Potato slices were fried in pure vegetable oil at 140° C. to a moisture content of 2%. Agtron (model E-15) colour scores were obtained for all chip samples. Agtron scores measure reflectance hence the darker the chip colouration, the lower the Agtron score. Agtron colour scores of less than 50 indicate unacceptable colouration of the chips Coffin et al., supra. Agtron scores are depicted graphically in FIG. 4.

EXAMPLE 3

DSC of Potato Cultivars/Selections

Starch gelatinisation studies were performed using differential scanning calorimetry (DSC) using Dupont Model 1090 thermal analyser equipped with a model 910 differential scanning calorimeter or a 2000 thermal analyser with a model 2910 DSC cell. The Interactive DSC Data Analysis Program "Heats and Temperatures of Transition—Version 3.0" (Dupont Instruments, Wilmington, Del.) was applied to all thermal curves to obtain the onset ($T_o$), peak ($T_p$) and final ($T_m$) temperatures.

Potato cultivars/selections were grown and harvested as in Example 1. Tissue samples were prepared for analysis by excising intact tissue from the permedullary zone of tubers using a 3 mm internal diameter cork borer Leszkowiat, M. J. et al., (1990) Journal of Food Science (in press). Bores were sliced using a razor blade and approximately 10 mg quantities were hermetically sealed in aluminum DSC pans. For isolated starch, approximately 3 mg of accurately weighed starch and 10 µl of water were hermetically sealed in aluminum DSC pans Hoover et al., supra. A DSC pan with 8 mg of sand and 2 mg of distilled water served as the reference. Samples were heated from 20° C. to 100° C. at a rate of 10° C. per min. Indium and benzoic acid were used for calibration for each heating rate. The volume fraction ($v_1$) of the samples was calculated as the ratio of the total volume of water to that of starch and water, with the density of water taken as 1.00 and that of starch as 1.50 Biliaderis, C. G. et al., (1986) *J. Agricultural Food Chemistry*, vol. 34, p. 6. Analysis was performed in triplicate.

The Statistical Analysis System ANOVA procedure (SAS, 1985) was used to perform analyses of variance and Duncan's new multiple-range tests. When indicated, levels of significance are $P \leq 0.05$.

The thermal parameters are set out in Table 1 for potato tissue from listed cultivars/selections.

When DSC was performed on isolated and intact starch preparations from the same cultivars/selections, rather than on potato tissue, similar results were obtained.

If analysis is to be performed on growing potato tubers before maturity is reached, isolated and intact starch preparations should be used as the higher prematurity sugar content of the potatoes interferes with the DSC values obtained if whole potato tissue is used.

Intact starch granules were isolated according to the method of Fishwick and Wright (1980) Phytochemistry, Vol. 19, p. 55 with the following modifications: Amyloplasts were allowed to settle in the column for 1.5 hours and collected in a detachable ampoule. Amyloplasts were then washed with distilled water ($\times 4$) and subsequently oven-dried at 30° C. for 24 hours prior to analysis.

EXAMPLE 4

Relationship Between $T_p$ and Chip Colour Score

Figure 5:
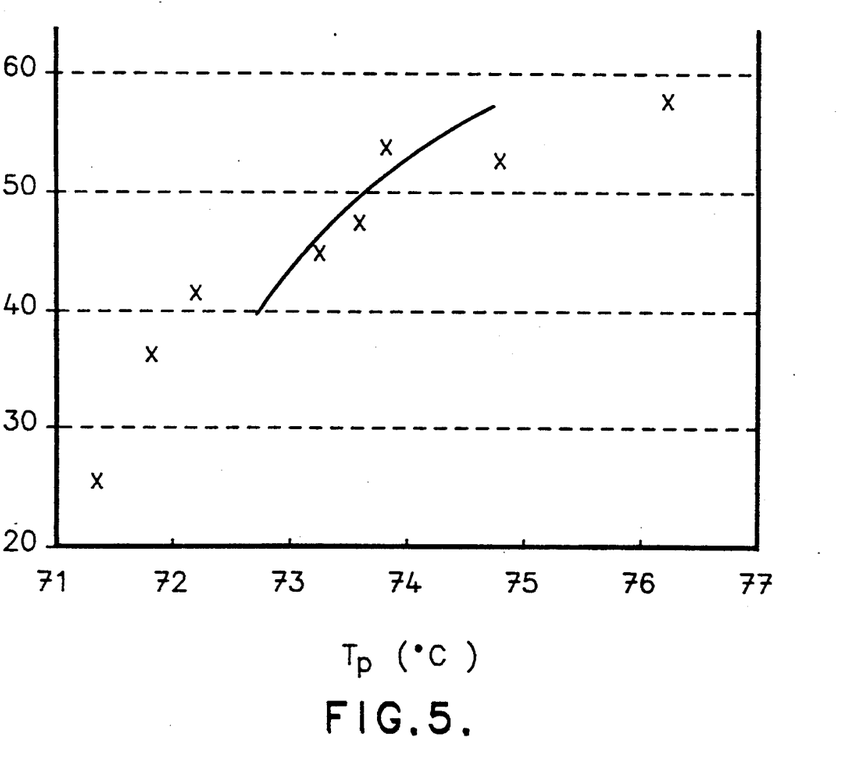
FIG. 5 shows a graph of average Agtron values plotted against peak temperatures.

The average Agtron value for each cultivar/selection (mean of Agtron values of FIG. 4) was compared with the $T_p$ value of that cultivar/selection (as determined in Example 3) as shown in FIG. 5, which is a graphical depiction of the data of Table 2.

There was a high degree of correlation between peak temperature, $T_p$ and average Agtron score ($r = 0.911$, $p \leq 0.01$) indicating that higher granule stability, as measured by peak temperature, $T_p$, is closely associated with resistance to chill-sweetening, resulting in lower sugar levels and acceptable colour scores.

As indicated above, an Agtron colour score of less than 50 indicates an unacceptable degree of chip colouration. Based on the data of Table 2 and the best curve calculated for the points of FIG. 5, the minimum acceptable $T_p$ for satisfactory chip preparation, corresponding to an Agtron score of 50, is $T_p$ of 73.7° C.

Although only certain embodiments of the present invention have been described, the present invention is not limited to the features of these embodiments but includes all variations and modifications within the scope of the claims.

REFERENCES

1. Pollock, C. J. and ap Rees, T. (1975) Phytochemistry, Volume 14, page 613.
2. Barichello, V., Yada, R. Y., Coffin, R. H. and Stanley, D. W., (1990) Journal of Food Science, Volume 55, page 1060.
3. Stevens, D. J. and Elton, G. A. H. (1971) Die Starke, Volume 23, page 8.
4. Wootton, M. and Bamunuarachchi, A. (1979A) Starch-Starke Volume 31, page 201.
5. Wootton, M. and Bamunuarachchi, A. (1979B) Starch-Starke Volume 31, page 262.
6. Donovan, J. W. (1979) Biopolymers, Volume 18, page 263.
7. Biliaderis, C. G., Maurice, T. J. and Vose, J. R. (1980) Journal of Food Science, Volume 45, page 1669.
8. Maurice, T. J., Slade, L., Sirett, R. R. and Page, C. M. (1985) in "Properties of Water in Foods", (Eds) Simatos and Multon page 211.
9. Lund, D. B. (1983) in "Physical Properties of Foods" (Eds.) Peleg & Bagley.
10. Leszkowiat, M. J. (1988) M. Sc. Thesis, University of Guelph.
11. Hoover, R. and Sosulski, F. (1985) Staerke, Volume 37, page 181.
12. Coffin, R. H., Yada, R. Y., Parkin, K. L., Grodzinski, B. and Stanley, D. W., (1987) Journal of Food Science, Volume 52, page 639.
13. Wilson, A. M., Work, T. M., Bushway, .A. A. and Bushway, R. J. (1981) Journal of Food Science, Volume 46, page 300.
14. Leszkowiat, M. J., Yada, R. Y., Coffin, R. H., and Stanley, D. W., (1990) Journal of Food Science (in press).
15. Biliaderis, C. G., Page, C. M., Maurice, T. J. and Juliano, B. O. (1986) J. Agricultural Food Chemistry, Volume 34, page 6.
16. Fishwick, M. J. & Wright, A. J. (1980) Phytochemistry, Volume 19, page 55.

The embodiments of the invention in which an exclusive property or privilege is claimed are defined as follows:

1. A method of determining the chipping suitability of starch-containing vegetables based on the quality of product to be derived from said vegetables when exposed to a chipping process that may result in undesirable product colouration due to chemical changes of surface sugars on the chipped product, which method comprises measuring the starch granule crystallinity of said vegetables, comparing said crystallinity measurements with a predetermined minimum level of starch granule crystallinity, and selecting the vegetable having the measured starch granule crystallinity above said predetermined minimum level whereby a vegetable product having an acceptable level of colouration during the chipping process is obtained.

2. A method of determining the susceptibility of vegetables to chill sweetening which comprises measuring the starch granule crystallinity of said vegetables, comparing said crystallinity measurements with a predetermined minimum level of starch granule crystallinity, and selecting the vegetable having the measured starch granule crystallinity above said predetermined minimum level whereby a vegetable having an acceptable level of chill sweetening resistance is obtained.

3. A method according to claims 1 or 2 the measuring step comprises the following steps
    (a) obtaining a starch-containing tissue sample from said vegetables; and
    (b) performing differential scanning calorimetry on said tissue sample.

4. A method according to claims 1 or 2 the measuring step comprises the following steps:
    (a) obtaining a starch-containing tissue sample from said vegetables;
    (b) isolating the starch from said tissue sample; and (c) performing differential scanning calorimetry on said isolated starch.

5. A method for detecting starch-containing vegetables that are resistant to chill sweetening based on the quality of product to be derived from said vegetables when cooked in a manner which can result in undesirable product colouration due to chemical changes of surface sugars on the prepared product, a predetermined minimum level of starch granule crystallinity being established for said vegetable to be cooked, above which minimum level an acceptable quality of cooked product having an acceptable level of colouration is assured, said method comprising:
   (i) measuring starch granule crystallinity of said vegetable to be cooked; and
   (ii) selecting for later cooking said vegetable having said measured starch granule crystallinity above said predetermined minimum level by virtue of said selected vegetable having said measuring starch granule crystallinity of said minimum level resisting chill sweetening.

6. A method of claim 5 wherein said starch granule crystallinity is determined by differential scanning calorimetry where peak temperature is a determining factor of said starch granular crystallinity.

7. A method of claim 6 further comprising determining said minimum level of starch granule stability by:
   (i) obtaining several starch-containing tissue samples from several vegetables of a type to be cooked;
   (ii) measuring peak temperature of each of said several samples by differential scanning calorimetry;
   (iii) cooking each of said several vegetables to form a cooked product, inspecting each cooked product of said several vegetables and selecting product of acceptable and unacceptable quality to develop a range of peak temperatures corresponding to levels of starch granule stability; and
   (iv) selecting cooked product of marginally acceptable quality whereby said minimum level of starch granule stability is determined by peak temperature corresponding to such marginal product.

8. A method of claim 7 for detecting chill sweetening resistance of potatoes for processing into a variety of potato products by deep frying or baking and further comprising:
   (i) removing a core sample of potato from a representative potato of a batch to be processed;
   (ii) subjecting said core sample to differential scanning calorimetry to determine said peak temperature; and
   (iii) selecting said batch of potatoes subject to said peak temperature being equal to or greater than said minimum peak temperature.

* * * * *